US008652093B2

(12) United States Patent
Lee et al.

(10) Patent No.: US 8,652,093 B2
(45) Date of Patent: Feb. 18, 2014

(54) SYSTEM FOR PROGRAMMING MEDICAL PUMPS WITH REDUCED-ERROR

(75) Inventors: Chaoyoung Lee, Weston, MA (US); Mei Zhang, Sharon, MA (US)

(73) Assignee: Zyno Medical, LLC., Natrick, MA (US)

( * ) Notice: Subject to any disclaimer, the term of this patent is extended or adjusted under 35 U.S.C. 154(b) by 13 days.

(21) Appl. No.: 13/526,212

(22) Filed: Jun. 18, 2012

(65) Prior Publication Data

US 2012/0323170 A1 Dec. 20, 2012

Related U.S. Application Data

(60) Provisional application No. 61/498,855, filed on Jun. 20, 2011.

(51) Int. Cl.
*A61M 31/00* (2006.01)

(52) U.S. Cl.
USPC .......................................... 604/67

(58) Field of Classification Search
USPC ............................................. 604/67, 131, 151
See application file for complete search history.

(56) References Cited

U.S. PATENT DOCUMENTS

| 7,515,060 B2* | 4/2009 | Blomquist ............... 340/692 |
| 7,785,463 B2* | 8/2010 | Bissler et al. ............ 210/143 |
| 8,515,547 B2* | 8/2013 | Mass et al. ............... 607/60 |
| 2005/0277872 A1* | 12/2005 | Colby et al. ............ 604/67 |
| 2011/0092907 A1* | 4/2011 | Krogh et al. ............ 604/151 |

\* cited by examiner

*Primary Examiner* — Aarti B Berdichevsky
(74) *Attorney, Agent, or Firm* — Boyle Fredrickson, S.C.

(57) ABSTRACT

Medical pumps may obtain programming data from a database through the use of a remote query process which allows the individual pump to flexibly request data from existing hospital databases, to identify the necessary information in those databases, and to convert that data for use without the need for manual programming or a centralized pump control system.

16 Claims, 4 Drawing Sheets

SYSTEM FOR PROGRAMMING MEDICAL PUMPS WITH REDUCED-ERROR

CROSS-REFERENCE TO RELATED APPLICATION

This application claims the benefit of U.S. Provisional Application No. 61/498,855 filed Jun. 20, 2011, entitled: Infusion Management System and Method and hereby incorporated by reference.

BACKGROUND OF THE INVENTION

The present invention relates to medical pumps for the delivery of medicines to patients under controlled rates and dosages and in particular to a pump allowing pump-initiated synchronization with existing medical databases for programming with reduced error.

Medical pumps, such as syringe pumps or peristaltic infusion pumps, are known for computer-controlled delivery of medication or contrast agents (henceforth drugs) to patients over a period of time. Typically the drug is delivered in a syringe (for a syringe pump) or a flexible bag (for peristaltic infusion pump, or ambulatory pump) that may be connected to an IV line attached to a needle for insertion into the patient. When a nurse or other health care professional ministering to the patient receives the drug, the healthcare professional reviews the drug description for correctness and enters the desired dose and rate into the pump. Other pump parameters such as alarm limits and the like may also be programmed at this time. The syringe or IV line must then be mechanically connected to the pump mechanism and the mechanism activated to begin pumping.

The process of programming pumps can be time-consuming and prone to error. In a large facility, there may be multiple different pump designs and models and a given healthcare professional ministering to a patient may need to work with many different types of pumps each having their own programming in data entry systems.

It is generally known to provide for medical pumps having wireless data communication capabilities. Such pumps present the possibility of having programming performed remotely, for example, by data transmitted from a central "pump control system" managed by a pharmacist or the like.

There are a number of obstacles to practical implementation of such a system including the need for substantial capital investment in a central pump control system, the time and effort necessary to configure a complex network of medical pumps that may move between patients on a regular basis, and problems of compatibility among pumps of many different types from different manufacturers.

SUMMARY OF THE INVENTION

The present invention provides a system and method for transferring programming data from a central database to disparate medical pumps without the need for extensive modifications of the hospital information infrastructure. Rather than establishing a central pump control system for "pushing" data to the pumps, individual pumps (or proxy) may "pull" the data from a general-purpose database by initiating a database query, selecting among query results, and mapping the selected results to pump programming commands. In this way, a specialized data server for medical pumps is not required and data synchronizing pumps may be cost-effectively integrated into the system.

Specifically, the present invention provides a method of programming remote medical pumps that works by connecting a wireless device to a network communicating with a database providing information identifying patients to pump programming data related to treatment of the patient and communicating a search query from the wireless device over the network to the database to identify at least one given patient. Programming data related to the given patient is selected from the search results to include pump programming data linked to patients. The pump programming data is translated into data for controlling a medical pump and the medical pump is operated according to the translated data.

It is thus an object of at least one embodiment of the invention to provide a system in which individual medical pumps initiate a "pull" of necessary data from pre-existing databases thus avoiding the extensive infrastructure changes necessary to implement a "pushing" of the data to the pumps, for example, requiring the generation and maintenance of data tables linking pumps to patients and/or presenting compatibility issues with existing pumps.

The wireless device may be the medical pump and the medical pump may include a user interface providing data output to a user and receiving data input from the user for the purpose of querying the database and selecting the desired data.

It is thus a feature of at least one embodiment of the invention to provide the benefits of the present invention with as little as a single medical pump enabled to make the necessary queries. By incorporating the browsing and querying structure into the pump itself, rapid adoption of the improvement of the present invention may be realized.

The pump programming data may include at least one of infusion rate and infusion volume.

It is thus a feature of at least one embodiment of the invention to eliminate transcription errors in critical programmed pump values.

The method may display received patient identifying information and display at least one of patient identifying information and pump programming data on the medical pump.

It is thus a feature of at least one embodiment of the invention to permit verification of downloaded data by a skilled professional operating a remote medical pump.

A confirmation input from a user of the medical pump may be required after display of patient identifying information and or pump programming data before operation of the pump.

It is thus a feature of at least one embodiment of the invention to require confirmation of correct remote loading of data at a remote pump.

The invention may wirelessly transmit medical pump operating data indicating operation of the medical pump It is thus a feature of at least one embodiment of the invention to permit remote monitoring of pump condition using the same network channels established for the initial downloading of data.

In an alternative embodiment, the wireless device may be a computing device other than the medical pump further including a user interface providing data output to a user and receiving data input from the user and any of the steps of querying, selecting results of the query, and translating the received data that may be conducted through the user interface by a user of the medical pump, with the data ultimately transferred to the medical pump.

It is thus a feature of at least one embodiment of the invention to permit the present system to be implemented for medical pumps having limited processing capabilities through the use of a proxy device.

The wireless device may be selected from the group consisting of a desktop computer system, a portable computer system, and a cell phone.

It is thus a feature of at least one embodiment of the invention to allow great flexibility in implementing a proxy device including, for example, using mobile devices as the proxy device allowing a nurse or other health care professional the ability to move freely between pumps and patients.

Electronically transferring the received medical pump programming data to the medical pump may occur wirelessly through an agent device wirelessly communicating with the medical pump and the medical pump may be programmed with an address of the agent device for wirelessly communicating therewith.

It is thus a feature of at least one embodiment of the invention to permit the use of a proxy device without the need for fundamental changes in the existing institution information infrastructure. The imaging device allows the proxy device and pumps to be preprogrammed with known fixed addresses, for example.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

DETAILED DESCRIPTION OF THE PREFERRED EMBODIMENT

Figure 1:
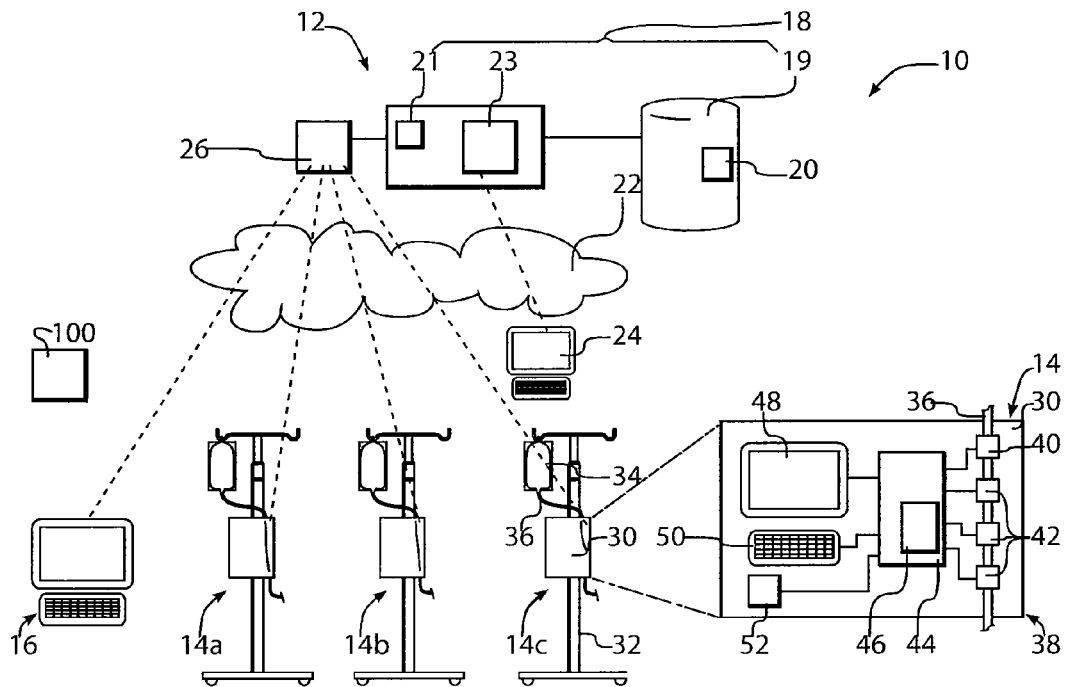
FIG. 1 is a block diagram of a medical pump system per the present invention providing wireless communication between medical pumps or a proxy and a standard medical database server showing various functional elements of the pump including an electronic controller executing a control program.

Referring now to FIG. 1, a medical infusion pump system 10 of the present invention may provide a file server system 12, one or more medical infusion pumps 14a-14c, and one or more standard proxy devices 16 such as a desktop computer, cell phone, PDA, tablet or the like.

The file server system 12 may be part of a standard hospital electronic medical record system and may include a memory system 19, for example, providing a disk array or the like. The memory system 19 may provide part of an electronic medical database 18 holding medical information and patient records and may include a drug dispensary database table 20 providing a listing of drugs and medical pump parameters for the delivery of those drugs to patients as linked to particular patient names for identification.

It will be understood that the database 18 provides both file structures on physical non-transient medium and also a program or database engine for accessing that data according to query instructions. In this regard, the database 18 may provide for a standard database interface, for example, using standard query language or a standardized API, and may further provide an interface accessible over a network. In one embodiment, the network interface may allow communication with the standard database interface using standard network interface conventions, for example, as may be implemented under HTML, XML or other well-known standards. The database engine and portions of the database 18 may be implemented by an electronic computer 21 being part of the file server system 12 executing a stored program 23 contained therein.

The file system 12 may communicate with a wireless network circuit 26 or the like that may implement a portion of a network 22, for example, providing standard wireless communication protocols such as IEEE 802.11 (a)/(b)/(g)/(n). The wireless network card may in turn communicate with corresponding wireless circuitry in each of the medical pumps 14a-14c as well as with a proxy device 16 as will be discussed below. The network 22 may also include physical media such as optical or electrical conductors.

The file server system 12 may connect via a network 22 with standard workstations 24 for use in a hospital or other health care setting. Such workstations 24, as is understood in the art, may access the database 18 through a standard browser program to generate search queries and to receive query responses that may be used to extract particular information from the database 18. Such file server systems 12 are normally pre-existing in a hospital environment as is necessary for the efficient management of patient information and hospital records independent of the present invention.

Referring still to FIG. 1, each medical pump 14 may provide, for example, a housing 30 that may be releasably attached to an IV pole 32, the latter that may support one or more bags of IV fluid 34 thereupon. The IV fluid 34 may be a saline solution or any of a number of intravenously administered medicines. An IV tube 36 may pass from the IV bag through a pump section 38 of the housing 30 of the pump 14 to be received by a peristaltic pump element 40 and one or more sensors 42, for example, including sensors for pressure of the IV fluid, flow rate of the IV fluid, air inclusion within the IV fluid, proper seating of the IV tube, and the like, all generally understood in the art. The IV tube 36 may then pass out of the pump section 38 to a needle assembly (not shown) for intravenous attachment to a patient.

Each of the pump element 40 and sensors 42 may connect to an internal controller 44 and execute a stored program 46 to provide control of the pump element 40 according to the program 46 and according to the readings of the sensors 42. The controller 44 may also communicate with user interface elements including a display screen 48 and a keypad 50 or the like, the latter including being provided by membrane switches, a touchscreen or the like. In addition, the controller 44 may communicate with a wireless network circuit 52 similar to the wireless network circuit 26 described above for communication over the network 22.

In an alternative embodiment, one or more of the medical pumps 14 may be a "syringe pump" or an ambulatory pump having similar features to the infusion pump described above, for the intravenous introduction of medicines and the like.

Figure 2:
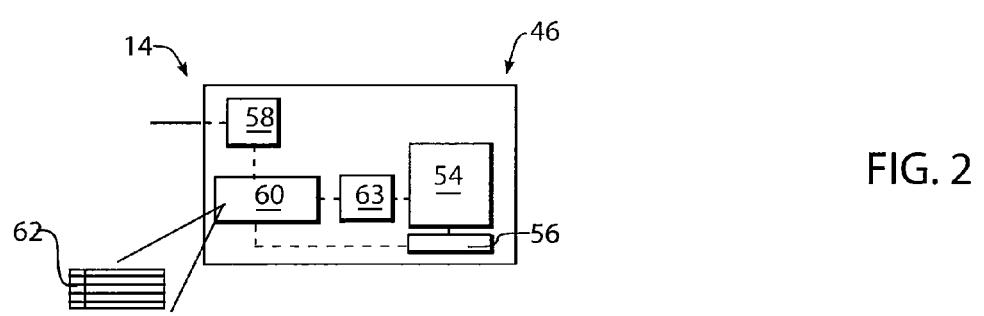
FIG. 2 is a block diagram of principal structures of a control program of the medical pump providing an ability to navigate the wireless network and to submit queries and respond to queries of network databases.

Referring now to FIG. 2, in a first embodiment, the program 46 may provide for a number of program elements including generally a pump control program 54 such as provides for the normal operation and control of the medical pump 14. The pump control program 54 may communicate with user interface routines 56 allowing the receipt of data from and transmission of data to the user interface formed by display screen 48 and keypad 50.

The program 46 may further include a network stack 58 for communication with the wireless network circuit 52 for receipt of data therefrom and transmission of data thereto. The network stack 58 may communicate with a query management routine 60 that may access a network table 62 to implement a connection to the database 18 and to manage simple queries of the database 18 to receive pump programming data from the database 18. The query management routine 60 may also communicate with the user interface routines 56 for receiving instructions therefrom related to queries or selection among query results and for displaying the results of queries and the like as will be described. In addition, the query management routine 60 may communicate with a translation routine 63 providing for translation of received programming data into a form compatible with the operation of the pump control program 54 for programming the same.

Figure 4:
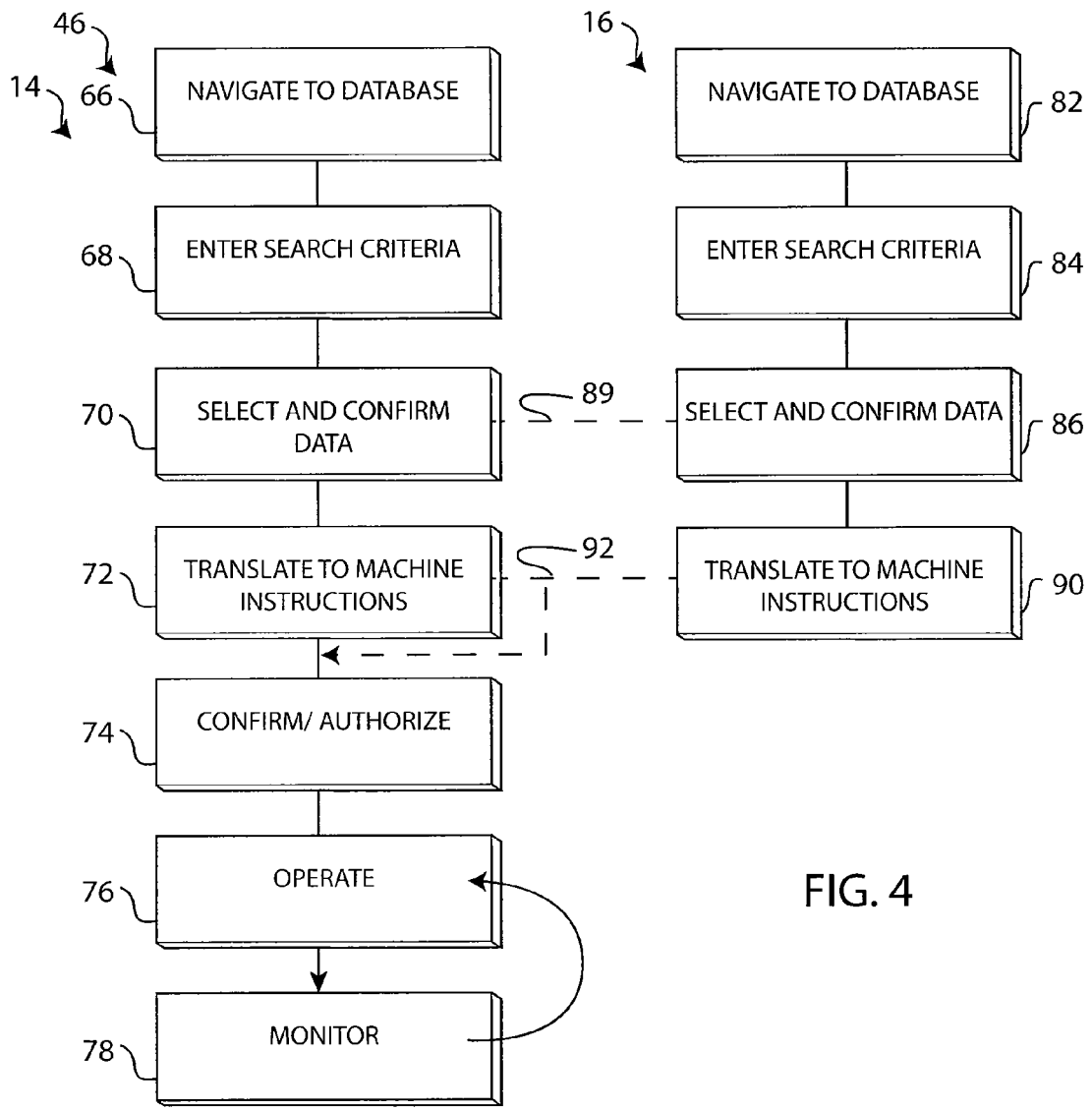
FIG. 4 is a flowchart showing steps of the present invention as may be implemented on the medical pump or on the medical pump and an associated proxy device.

Referring now also to FIGS. 1 and 4, the query management routine 60 operating with the network stack 58 allows a user to navigate over the network 22 (shown in FIG. 1) to access the database 18 as indicated by process block 66 of FIG. 4. In one embodiment, the navigation may be through the use of a browser that allows exploration of the network hierarchy by a user in an interactive manner, in the manner of a network or file directory tool. In this embodiment, the system may work on an ad hoc basis with a variety of different network types and configurations. In the event that the interface to the database 18 presents a webpage interface, the query management routine 60 may provide for the necessary interpretation and generation of web commands in HTML or XML necessary to communicate with that interface. In an alternative embodiment, the query management routine 60 may make use of the information previously stored in the network table 62 to go to a preassigned address determined to be that of the database 18.

It will generally be appreciated that the invention permits a connection to the database 18 that can be done with substantially no modification of the network 22 and file server system 12 (other than making the necessary connections to the network 22 incident to any wireless system) and thus may work immediately in a variety of hospital environments and can be practical for as little as a single pump 14 because of the relatively low fixed costs attendant to the system.

As indicated by process block 68 of FIG. 4, the query management routine 60 may then prompt the user through displaced screen 48 (shown in FIG. 1) to enter a patient name or other patient identification and may use that entered information as part of a search query to be provided to the database 18 over the network 22.

Importantly, the user need not enter information that uniquely identifies a patient but may enter a "sub-string" providing some data necessary to select a group of patients to which the patient of interest belongs which may then be individually identified. This ability to search for a sub-string allows the system to operate robustly without pre-configuration or the user having detailed configuration information.

Figure 5:
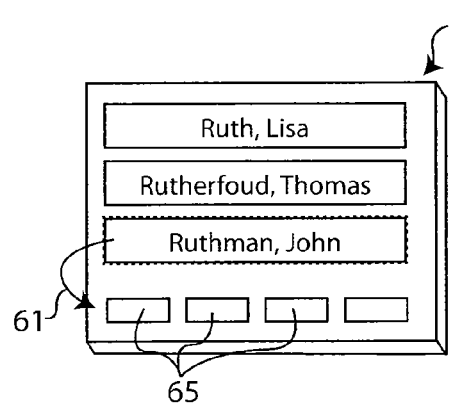
FIG. 5 is a representation of a screen that may be presented to the user of the medical pump displaying the results of the search query, allowing selection of one such result, and mapping that result to a pump control parameter.

Accordingly, at process block 70, results of that search may be returned from the database 18 over the network 22 and displayed to the user on screen 48, may present multiple search results, for example, as shown in FIG. 5 representing several patients meeting the sub-string search criteria. In this example, the user may have entered as patient identification information the first four letters of the last name of the patient (e.g. "Ruth") to receive back a search query consisting of the names of "Ruth", "Rutherford", and "Ruthman" each of which may be displayed to the user. The invention contemplates that there may also be multiple patients with the same last name. It will be appreciated that this process need not use the patient name but may use any patient identifier including a portion of their patient ID or the like.

The user may then select a given patient from this list using the keypad 50 (shown in FIG. 1), the selection of which serves as a first level of confirmation of the correctness of the patient identity as well a selecting among multiple query responses. It will be appreciated that the ability to select among query responses also allows the system of the present invention to work without prior set up between the medical pump 14 and the file server system 12 or linking between a pump 14 and a given patient.

This selected response may be then provided to the query management routine 60 to formulate a new query intended to provide not simply patient names but a full listing of pump control information contained in the drug dispensary database 18. Alternatively, the selected response may simply access specific data already downloaded with the query results. In either case the data associated with the selected query response may need reformatting to be compatible with the program settings of the medical pump 14 and may need to be identified to a particular program setting of the medical pump 14. In this latter regard, the user may drag the selected response as indicated by arrow 61 of FIG. 5 to a target 65 identifying a needed program setting of the medical pump 14. This dragging process will provide the necessary reformatting or translation of the received data based on the needs of the target 65 as indicated by process block 72. In a simple case, the translation may be a range adjustment or truncation of precision and may be performed by a simple script of translation routine 63 (shown in FIG. 2) that may work with a wide variety of database formats and/or which may be customized to a particular database format. The values received by the target 65 then provide the control parameters used by the pump control program 54 (e.g. pump flow rate, delivery volume, alarm settings and the like). In an extremely simple version the translation process may be performed by a transcription of the data by the user.

It will be appreciated that the translation process of process block 63 allows a post hoc use of data of the database 18 by the pump 14 and also enlists the user both in verifying the data and mapping the data so that the invention may work with a wide variety of different pump types and different database organizations. To the extent that their idiosyncrasies in the way necessary pump data is stored in the database 18, these idiosyncrasies may accommodate modification of the program of the pump 14 and thus do not require a change to the hospital information infrastructure and in particular the format of the database 18.

Figure 6:
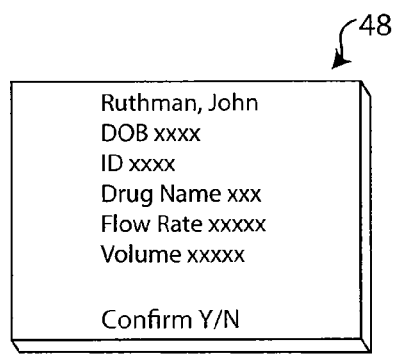
FIG. 6 is a figure similar to that of FIG. 5 showing a display of downloaded pump control parameters for confirmation, organization, and validation.

Referring now to FIGS. 4 and 6, the query management routine 60 may present the data that that will be used by the pump 14 on the display screen 48 (shown in FIG. 1) for review by the user (typically a nurse or physician) attending the patient. This display allows for confirmation by the user. Upon receipt of that confirmation, per process block 74, which may be entered, for example, by the pressing of a button or the entry of a code number through a keypad 50 or the like, the medical pump 14 is fully programmed and may be activated by an additional command to operate to dispense medicine as indicated by process block 76.

It will be appreciated that the above described process reduces or eliminates errors in programming of the pump 14 and may be used to program alarm parameters as well as drug delivery parameters, including as noted: flow rates, drug volumes, total delivery time and volume, and the like. The above described process may provide convenience and save time by reducing key strokes when manually programming a pump through pump keypad, which is a conventional practice.

During the operation of the pump 14 per process block 76, the same wireless network 22 and the established connection may be used to report out particular alarm conditions and operating status of the machine as indicated by process block 78. The status may include, for example, problems detected in the delivery of the drug, for example, by sensors 42 described above with respect to FIG. 1, the activation of alarm conditions or the like. Other remote control of the pump 14 through the network is also possible.

Figure 3:
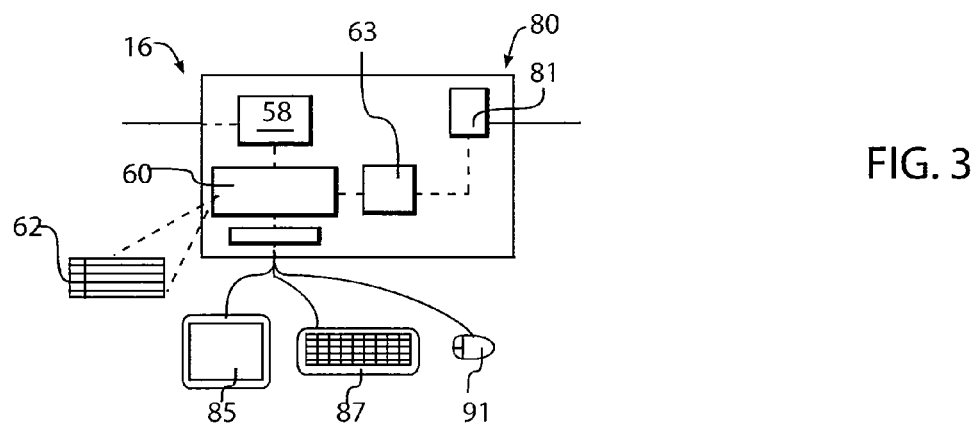
FIG. 3 is a block diagram similar to FIG. 2 of principal structures of a program of a proxy device that may work with the medical pump of FIG. 2 in implementing the present invention in an alternative embodiment.

Referring now to FIGS. 1, 3 and 4 in an alternative embodiment, limitations in the computational or hardware capability of the pump 14 (for example needed to support the network connection query generation and mapping process) may be accommodated through the use of a proxy device 16 typically nearby the medical pump 14 and communicating therewith either through a wired or wireless connection. Alternatively, the proxy device 16 may be integrated into the medical pump 14, for example, in a docking cradle with an interfacing electrical connector removably holding, for example, a tablet or smart phone, as described below.

The proxy device 16 may also provide a processor executing a stored program 80 implementing many of the functions of program 46 including, for example, providing functions of the network stack 58, the query management routine 60, the network table 62 and optionally the translation routine 63.

Per process block 82, using the program 80, the user may navigate to the database 18 per process block 82, for example, as guided by output to a display 85 and instructions provided by the user per a keyboard 87 and mouse 91 or the like (such as a touch screen). Again as discussed with respect to process block 68 above, the user may enter a search query at process block 84 and receive at process block 86 the results of that query to identify and confirm a particular patient and to receive associated pump programming information from the database 18.

In one embodiment, this pump programming information may then be conveyed directly to the pump 14 as indicated by dotted line 89. Under this approach, information may be transmitted from the proxy device 16 to the pump 14 or the user may provide to the server system 12 a pump identification number so that the results from the search criteria go directly to the pump 14. Alternatively, the translation process may be conducted on the proxy device 16 as indicated by process block 90 and the translated and mapped instructions transferred to the pump 14 as indicated by dotted line 92.

Referring momentarily to FIG. 3, this transfer may be affected through the wireless network circuit 52 or through another communication protocol stack 81, for example Bluetooth communication or direct cabling, communicating with comparable hardware in the medical pump 14.

In both of the above examples, the authorization step of process block 74 on the pump 14 is preserved as are the step of process block 76 and optionally of process block 78.

Figure 7:
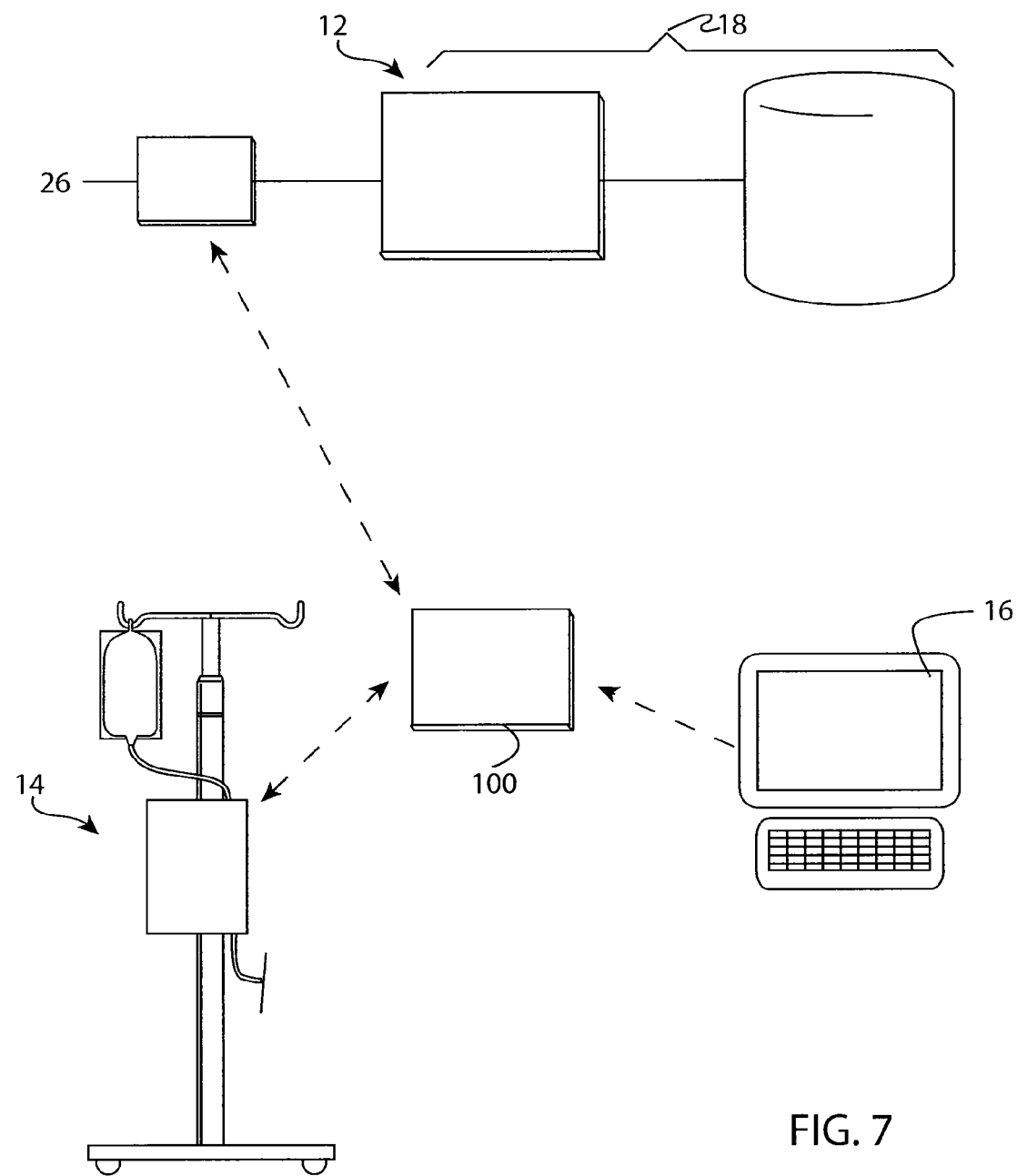
FIG. 7 is a figure illustrating an agent device wirelessly communicating with a medical pump, a proxy device, and wireless network circuit.

In the above examples, the communication between the pump 14 and the file server system 12 may be conducted through an agent device 100, for example, providing a standard address preprogrammed into each of the pumps 14. As illustrated in FIG. 7, the agent device 100 may then implement a router type function to communicate with the necessary address of the file system 12 and database 18. In this way, each of the pumps 14 may be preprogrammed with only the address of the agent device 100 and the agent device 100 may be programmed independently, for example, using a more convenient user interface and a more powerful processing circuit. For example, the agent device 100 may be a standard desktop computer or the like including, for example, a computer implementing the proxy device 16. The agent device 100 may likewise implement some of the steps of the proxy device 16.

Significantly, the agent device 100 may be used to provide for the communication of data between the proxy device 16 and the pump 14 when the proxy device 16 is used. For example, in one embodiment, the transfer of data to the pump 14 from the server system 12 (and hence from the database 18) may be received by the proxy device 16 and transferred to the agent device 100 and then to the pump 14. Alternatively, the data from the server system 12 intended for the proxy device 16 may be intercepted by the agent device 100 to be transmitted to the pump 14. In this latter case, all communications via the proxy device 16 may pass through the agent device 100. Again this provides a uniformity of communication addresses for the pump 14 and agent device 100 and further allows the existing hospital file server system 12 to be used without modification or substantial modification. This elimination of the need to modify the existing information infrastructure of the hospital both simplifies the use of the present invention and allows its incremental adoption without the need to overcome substantial fixed capital costs.

Figure 8:
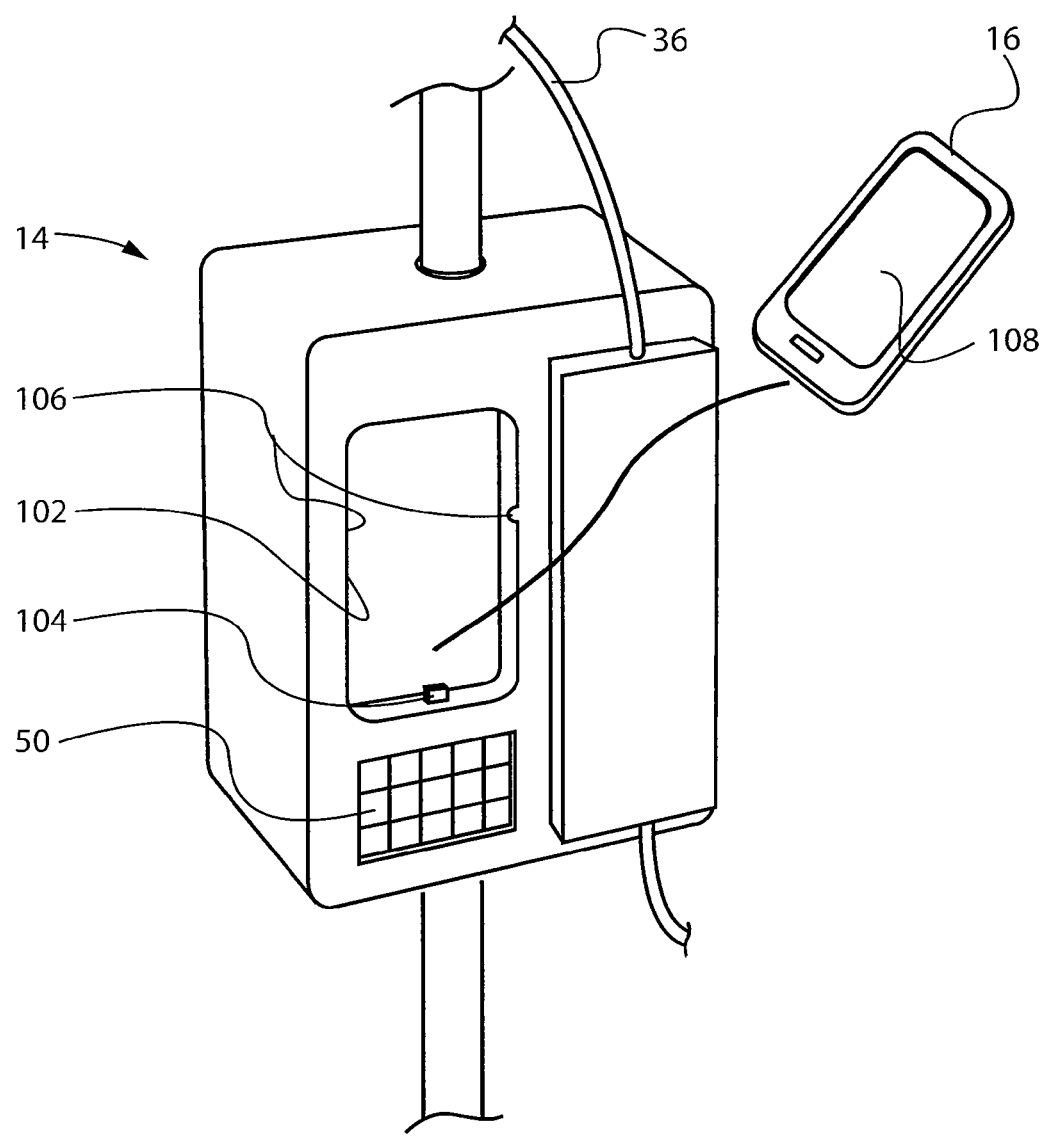
FIG. 8 is a fragmentary perspective view of an infusion pump per the present invention providing a socket for receiving a smart phone or the like therein to provide a proxy device per FIG. 3.

Referring now to FIG. 8, the proxy device 16, in the form of a smart phone or tablet, may be received within a socket 102 formed in a front panel of an infusion pump 14 to engage with an electrical connector 104 on the infusion pump 14 within the socket 102 and providing direct electrical communication between the pump 14 (e.g. the controller 44) and the proxy device 16. As is generally understood in the art, a table and/or smart phone will generally have wireless capabilities, a data exchange socket, and full user interface including typically a touch screen display driven by an internal processor having local memory. The socket 102 may further provide mechanical retention elements 106 releasably holding the proxy device 16 therein. Optionally, the communication between the pump and proxy device may be wireless, for example, by a Bluetooth connection.

As so installed in the pump 14, the proxy device 16 may present a front facing data entry and display screen 108 (for example, a touch screen) allowing the user to enter the search strings described above. In this regard, it will be appreciated that the proxy device 16 may communicate wirelessly with the file system 12 through the wireless network circuit 26 and may provide a conduit for the received programming data passed from file system 12, through the proxy device 16, to the pump 14 through the connector 104. Generally, the proxy device 16 will not control actual pump functions which will be controlled instead by the internal pump controller 44 described above with respect to FIG. 1.

A special application program running on the proxy device 16 communicating with the browser on the proxy device 16 may be used to communicate through connector 104 the required data. Additional controls 50 may also be provided to allow full functionality of the pump 14 without the proxy device 16.

In application, for example, the proxy device 16 may be used either free from the pump 14 or when connected to the pump 14 to make the connections to the file system 12 and to obtain the necessary pump programming information. The application program running on the proxy device 16, may require that the proxy device 16 be installed in the pump 14 for inputting some pump specific information such as drug type and/or confirming patient identification and other matters and for downloading the pump programming information to the pump 14. In this respect, the pump 14 may communicate a unique pump identifier number to the proxy device 16 that may be used to ensure correct matching of pump and programming information to a patient. Attaching the proxy device 16 to the socket 102 may help reduce programming errors that could occur when using a highly mobile device by providing a physical reminder of the particular pump being program. The connector 104, in addition to transferring data may provide power to the proxy device 16. The proxy device 16 may provide for ancillary or improved interface functionality in the pump 14, for example, to provide reporting functions from the pump 14 to the file system 12 and storing data therefrom.

It will be appreciated that the invention allows the actual pump programming data to be transmitted electronically eliminating the possibility of keystroke errors or the like.

Patient date of birth/voice recognition/partial search and search results allow flexible identification of the records regardless of precise indexing.

Example I

A patient comes to a clinic for an infusion treatment ordered by her doctor. A care giver (such as a nurse) inputs the last 4 digits of the patient identification into a pump and initiates an inquiry for all infusion orders created for this patient within the organization. The pump communicates with a database through a server to search for all infusion orders that meet the searching criterion (e.g. infusion orders where the last 4 digits of patient identification matches what the nurse has input). The searching criterion can be refined at the server, for example, because the inquiry comes from a pump, or a device that associated with a pump, and the search will be conducted for all infusion-related orders, not other information such as prescriptions of medicines that needs to be taken orally.

Infusion orders populating the database can be generated by a pharmacist and saved previously in the database through a server application programming interface, or by a printer that automatically sends all information related to dispensed drugs to the database when the order is printed. This process can be done by customizing the printer driver file.

The search results from a database are then returned to the pump or other devices associated with the pump through a server system. The returned searching results could be a list of infusion orders with patient identification ending with the same 4 digits the nurse input. The returned infusion orders can be for the same patient or different patients. The nurse reviews the resulting orders, further refines the search by verifying the entire name and date of birth of the specific patient, then selects one or more infusion orders to execute.

If the resulting order is found, the nurse can convert the order to a pump programming code and send it to the pump. The details of the order, such as flow rate, volume to be infused, infusion time, and maximum allowable flow rate for this drug, etc., can be displayed on the pump for the nurse to verify before executing. At this point, the nurse can also change the parameters if necessary.

The nurse authorizes the execution of a specific order after confirmation of the correctness of the infusion task. The nurse can also monitor the execution of the selected/programmed infusion order directly on the pump or remotely through a server. Related infusion information can be stored on a database, and may be processed in real time or retrospectively. The completed infusion task can be reported by the pump or other devices on behalf of the pump for administrative purpose, such as bill paying management.

Example II

A pump user can input the searching criterion (criteria) from a computer separate from the pump. As in the searching criterion in Example I, the nurse can input the last 4 digits of the patient identification into a computer and initiate an inquiry for all infusion orders created for this patient within the organization, and request the results to be displayed on the pump by inputting a pump identification number. A server performs the search from relevant data source and returns the results to the pump as identified.

Example III

A pump user can input the searching criterion (criteria) from a mobile device such as a tablet or cell phone. As in the searching criterion in Example I, the nurse can input the last 4 digits of the patient dedication into a mobile phone and initiate an inquiry for all infusion orders created for this patient within the organization, and request the results to be displayed on the pump by providing the pump identifier, or displayed on both the phone and the pump. A server serves as an agent and performs the search from relevant data source and returns results to the pump using the pump identifier. This method enables home care pump users to obtain patient specific infusion orders wirelessly through mobile phones. The user can refine the search results and authorize execution of an infusion tasks after final selections and/or modifications.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A method of programming remote medical pumps using a medical pump including a housing, a pump mechanism supported by the housing and providing a pump adapted to work with an IV line together with at least one sensor sensing a parameter of material flowing through the IV line, a wireless network circuit, an electronic controller supported by the housing and communicating with the wireless network circuit, the pump and at least one sensor, the electronic controller executing a program stored in non-transitory computer readable storage medium to: (a) connect to a wireless network; (b) communicate over the wireless network to submit a search query to a database on the wireless network providing a patient identification; (c) display a search query result of at least one patient to a user to receive input from the user to select a given patient from the search query result; (d) receive pump programming data from the database related to the given patient; (e) convert the pump programming data into data for controlling the medical pump; and (f) operate the medical pump according to the converted data, the method comprising the steps of:
   (a) connecting a wireless device to a network communicating with a database providing information identifying patients to pump programming data related to treatment of the patient;
   (b) communicating a search query from the wireless device over the network to the database to identify at least one given patient;
   (c) receiving search results from the database at the wireless device, the search results including pump programming data linked to patients;
   (d) selecting pump programming data related to the given patient;
   (e) converting the pump programming data into data for controlling a medical pump; and
   (f) operating the medical pump according to the converting data.

2. The method of claim 1 further including the step of wirelessly transmitting medical pump operating data indicating operation of the medical pump.

3. The method of claim 1 wherein the wireless device is the medical pump and further including a user interface providing data output to a user and receiving data input from the user and wherein steps (b)-(e) are conducted through the user interface by a user of the medical pump.

4. The method of claim 3 wherein the pump programming data includes at least one of infusion rate and infusion volume.

5. The method of claim 1 further including the step of receiving patient identifying information and pump programming data from the database and displaying at least one of patient identifying information and pump programming data on the medical pump prior to step (f).

6. The method of claim 5 further including the step of requiring a confirmation input from a user of the medical pump after step (d) and before step (f).

7. The method of claim 1 wherein the wireless device is a computing device other than the medical pump further including a user interface providing data output to a user and receiving data input from the user and wherein steps (b)-(d) are conducted through the user interface by a user of the medical pump and including the step of electronically transferring the received pump programming data to the medical pump.

8. The method of claim 7 wherein the step of electronically transferring the received pump programming data to the medical pump occurs wirelessly through an agent device wirelessly communicating with the medical pump and wherein the medical pump is programmed with an address of the agent device for wirelessly communicating therewith.

9. The method of claim 7 wherein the wireless device is selected from the group consisting of a desktop computer system, a portable computer system, and a cell phone.

10. The method of claim 9 wherein the wireless device is removably attached to the medical pump.

11. A medical pump comprising:
   a housing
   a pump mechanism supported by the housing and providing a pump adapted to work with an IV line together with at least one sensor sensing a parameter of material flowing through the IV line;
   a wireless network circuit;
   an electronic controller supported by the housing and communicating with the wireless network circuit, the pump and at least one sensor, the electronic controller executing a program stored in non-transitory computer readable storage medium to:
   (a) connect to a wireless network;
   (b) communicate over the wireless network to submit a search query to a database on the wireless network, the search query providing a patient identification;
   (c) in response to (b), display a search query result of at least one patient to a user to receive input from the user to select a given patient from the search query result;
   (d) in response to (c), receive pump programming data from the database related to the given patient selected by the user;

(e) convert the pump programming data into data for controlling the medical pump; and
(f) operate the medical pump according to the converted data.

12. The medical pump of claim 11 wherein the electronic controller executes the program to receive patient identifying information from the database and display the received patient identifying information on the medical pump.

13. The medical pump of claim 11 wherein the electronic controller executes the program to require a confirmation input from a user of the medical pump after the pump receives pump programming data from the database.

14. The medical pump of claim 11 wherein the electronic controller executes the program to wirelessly transmit medical pump operating data indicating operation of the medical pump.

15. The medical pump of claim 11 further including a user interface providing data output to a user and receiving data input from the user and wherein steps (b)-(c) are conducted through the user interface by a user of the medical pump.

16. The medical pump of claim 15 wherein the pump programming data includes at least one of infusion rate and infusion volume.

* * * * *